United States Patent
Stuehle et al.

(10) Patent No.: US 9,931,020 B2
(45) Date of Patent: Apr. 3, 2018

(54) SURGICAL INSTRUMENT WITH A VIA

(71) Applicant: OLYMPUS WINTER & IBE GMBH, Hamburg (DE)

(72) Inventors: Sebastian Stuehle, Hamburg (DE); Sebastian Jungbauer, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 385 days.

(21) Appl. No.: 13/886,318

(22) Filed: May 3, 2013

(65) Prior Publication Data
US 2013/0303850 A1    Nov. 14, 2013

(30) Foreign Application Priority Data

May 8, 2012   (DE) .................. 10 2012 207 580

(51) Int. Cl.
*A61B 1/04*    (2006.01)
*A61B 1/06*    (2006.01)
(Continued)

(52) U.S. Cl.
CPC ........ *A61B 1/00142* (2013.01); *A61B 1/0011* (2013.01); *A61B 1/00071* (2013.01);
(Continued)

(58) Field of Classification Search
CPC ............. A61B 1/0011; A61B 1/00112; A61B 1/00114; A61B 1/00121; A61B 1/00124;
(Continued)

(56) References Cited

U.S. PATENT DOCUMENTS 6,080,101 A * 6/2000 Tatsuno et al. ............... 600/112
7,074,181 B2   7/2006 Futatsugi
(Continued)

FOREIGN PATENT DOCUMENTS

DE    10 2006 015 176 B3    7/2007
DE    10 2006 054 249 A1    5/2008
(Continued)

OTHER PUBLICATIONS

English Abstract of EP 1923099 A1, dated May 21, 2008.

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

A surgical instrument, such as an endoscope, having a hermetically sealed housing for accommodating, optical and/or electrical devices therein. The housing having a wall with a via provided in the wall to electrically connect an electrical contact formed on the inside of the wall with an electrical contact formed on the outside of the wall, wherein the via has a penetration in the wall, and the penetration is filled with a filling material to form a hermetically sealed housing, wherein the electrical contacts are formed as at least one electrically conductive conductor path on the inside of the wall and on the outside of the wall, wherein one conductor path on the inside of the wall, and one conductor path on the outside of the housing are connected to each other by means of the via, and wherein the filling material of the via consists of metal or solder.

20 Claims, 1 Drawing Sheet

(51) Int. Cl.
*A61B 1/00* (2006.01)
*G02B 23/24* (2006.01)

(52) U.S. Cl.
CPC ...... *A61B 1/00114* (2013.01); *A61B 1/00124* (2013.01); *G02B 23/2476* (2013.01)

(58) Field of Classification Search
CPC .......... H05K 1/00; H05K 1/02; H05K 1/0284; H05K 1/09; H05K 2201/09818; H05K 2201/09827; H05K 2201/09836; H05K 2201/09845; H05K 2201/09854; H05K 2201/09863
USPC ........ 600/109, 110, 112, 130, 132, 133, 160
See application file for complete search history.

(56) References Cited

U.S. PATENT DOCUMENTS

| | | |
|---|---|---|
| 2002/0139556 A1 | 10/2002 | Ok et al. |
| 2004/0105025 A1* | 6/2004 | Scherling ........... G02B 13/0015 348/335 |
| 2011/0313252 A1* | 12/2011 | Lin ............................... 600/162 |
| 2012/0034573 A1* | 2/2012 | Erdmann et al. ............... 433/29 |
| 2012/0197326 A1 | 8/2012 | Pavlovic |

FOREIGN PATENT DOCUMENTS

| | | |
|---|---|---|
| DE | 10 2011 009 856 A1 | 8/2012 |
| EP | 1 721 568 A1 | 11/2006 |
| JP | 200060793 A | 2/2000 |
| JP | 2004267351 A | 9/2004 |
| JP | 200661399 A | 3/2006 |
| JP | 2009231509 A | 10/2009 |
| WO | 2010023733 A1 | 3/2010 |

\* cited by examiner

SURGICAL INSTRUMENT WITH A VIA

CROSS-REFERENCE TO RELATED APPLICATION

The present application is based upon and claims the benefit to DE 10 2012 207 580.1 filed on May 8, 2012, the entire contents of which are incorporated herein by reference.

BACKGROUND

Field

The invention generally relates to a surgical instrument, especially an endoscope, more preferably a video endoscope, having a hermetically sealed housing for accommodating, preferably optical and/or electrical, devices within the interior of the housing, wherein the housing has a housing wall.

Prior Art

Such a surgical instrument is for example known from DE 10 2006 015 176 B3. The surgical instrument is provided as a rigid medical video endoscope with a system tube, wherein the system tube is provided distally with a window that accommodates an objective lens and a video camera in its distal end region and is connected to the outside by electrical lines through a proximal opening in the system tube, wherein the lines in the opening run through a seal consisting of a sealing compound.

Video endoscopes are designed elongated with a small cross-section. In generic video endoscopes, image sensors and the upstream lens systems are normally arranged in the distal region of the endoscope shaft, that is, in the region of the endoscope tip. Image signals and control signals are transmitted via the signal lines to or respectively from the proximal end, that is, the handle.

The autoclavability of the endoscope is an important requirement. During autoclaving, the endoscope is treated with hot steam under a high pressure. In the case of optical endoscopes and in particular video endoscopes, it is necessary to protect the optical components and the image sensor from steam which would otherwise condense on the lens system upon cooling and impair the optical quality of the system. Video endoscopes are therefore normally constructed in a hermetically sealed manner. The hermetic seal prevents steam from penetrating into the hermetically sealed region. With conventional video lens systems, this normally extends from the shaft tip into the handle.

Video endoscopes are generally designed elongated with a small cross-section due to their application, for example, for introduction into the body channels of a patient. Corresponding video endoscopes transmit video signals from the distally arranged video camera via electrical lines to a proximal end of the video endoscope, and the video signals are conducted to the outside through its housing with a contacting device. Between the contacting device and the video camera, the conductors or respectively lines run on an insulated conductor support.

SUMMARY

The object of the present invention is to provide a surgical instrument with a hermetic chamber, wherein especially the electrical cable bushing leading out of the hermetic housing of the instrument has a simple design.

This object is achieved with a surgical instrument, in particular an endoscope, more preferably a video endoscope, having a hermetically sealed housing for accommodating, preferably optical and/or electrical, devices within the interior of the housing, wherein the housing has a housing wall, that is further developed in that a preferably filled via (vertical interconnect access) is provided in the housing wall to electrically connect an electrical contact formed on the inside of the housing wall with an electrical contact formed on the outside of the housing wall, wherein the via has a penetration in the housing wall, and the penetration is filled with a filling material to form a hermetically sealed housing of the surgical instrument, wherein the electrical contacts are formed as at least one electrically conductive conductor path on the inside of the housing wall and as a least one electrically conductive conductor path on the outside of the housing wall, wherein one conductor path on the inside of the housing wall, and one conductor path on the outside of the housing wall are connected to each other by means of the via, and wherein the filling material of the via consists of metal or solder. An electrical connection from the hermetic interior of the housing is thereby formed to the outside of the housing interior.

The invention is based on the concept of forming or providing vertical electrical contacts that are also termed a via (vertical interconnect access) in a hermetically sealed housing of surgical instruments, wherein the vias are filled with a filling material. This type of electrical contact is termed a "plugged via." Since a contact, for example conductor path or line, in the interior of the housing is electrically connected to an outside contact on the outside of the housing, it is possible to achieve a hermetic signal transmission and simultaneously a hermetic seal of the housing wall or respectively housing. The hermetic lead through is formed by the via which is filled with a filling material such as plastic, metal or solder. The via in the housing wall is thereby directly connected to the conductor paths on the outside and inside of the housing wall such that, in addition to creating a basic housing body e.g. made of plastic or ceramic, the basic housing body is provided with conductor paths in the region of the via penetrations, and the penetrations will be or are correspondingly filled. Consequently, no additional procedural step is required for production.

In particular, the surgical instrument is designed as a video endoscope with an elongated, preferably hermetically sealed housing for accommodating an image sensor unit, especially a video camera, in the distal region of the housing, wherein one or more electrical lines connected to the image sensor unit are provided in the housing designed as an endoscope shaft. In particular, the via is formed in the region of the proximal end of the housing, preferably in the end region on a proximal face of the housing.

According to the invention, the embodiment of the surgical instrument provides that the electrical contacts are formed as at least one electrically conductive conductor path on the inside of the housing wall, and/or as at least one electrically conductive conductor path on the outside of the housing wall, preferably in the proximal end region of the housing, wherein in particular at least one conductor path on the inside of the housing wall and at least one conductor path on the outside of the housing wall are connected to each other by means of the via. In addition, it is possible within the scope of the invention to provide a plurality of conductor paths on the inside that are connected to corresponding conductor paths on the outside of the housing using the via. Furthermore in one embodiment, a plurality of adjacent vias are provided next to each other in the housing wall, wherein each filled via is connected in each case to one conductor path on the inside of the housing wall and to one conductor path on the outside of the housing wall.

In addition, the housing is preferably designed as an endoscope shaft, wherein the via is formed in the proximal end region of the endoscope shaft. A reliable signal transmission in the proximal end region of an endoscope or video endoscope is thereby achieved.

In addition, a further development of the surgical instrument is characterized in that the filling material in the penetration of the via is electrically conductive. For example, the filling material consists of a metal or solder.

Furthermore in one further development of the surgical instrument, in particular an endoscope, it is preferred that at least one conductor path is or will be formed on the inside of the housing wall using the MIP method (microscopic integrated processing method (MIPTEC)) and/or using the laser direct structuring method (LDS method), and/or that at least one conductor path is or will be formed on the outside of the housing wall using the MIP method and/or using the laser direct structuring method.

The electrical conductor paths can be applied on the surface of the inside of the housing wall, as well as on the outside of the housing wall, with conventional means, e.g. such as are known from MIPTEC (microscopic integrated processing technology). It is preferable to apply the conductor paths by means of a laser direct structuring method (LDS) as is, for example, offered by the company LPKF Laser & Electronics AG, Garbsen, Germany.

In particular in one further development of the surgical instrument, it is preferred to provide an additional conductor path for an optical image sensor unit arranged in the interior of the housing, in particular a video camera, such that the image sensor unit and the via are connected to each other, wherein in particular the additional conductor path is formed in the interior of the housing on the housing wall along a longitudinal extension of the housing. The housing of the surgical instrument is preferably manufactured of ceramic or plastic.

Further characteristics of the invention will become apparent from the description of the embodiments according to the invention together with the claims and the included drawings. Embodiments according to the invention can fulfill individual characteristics or a combination of several characteristics.

BRIEF DESCRIPTION OF THE DRAWINGS

The invention is described below, without restricting the general idea of the invention, using exemplary embodiments with reference to the drawings, whereby express reference is made to the drawings with regard to the disclosure of all details according to the invention that are not explained in greater detail in the text. In the figures.

DETAILED DESCRIPTION

Figure 1:
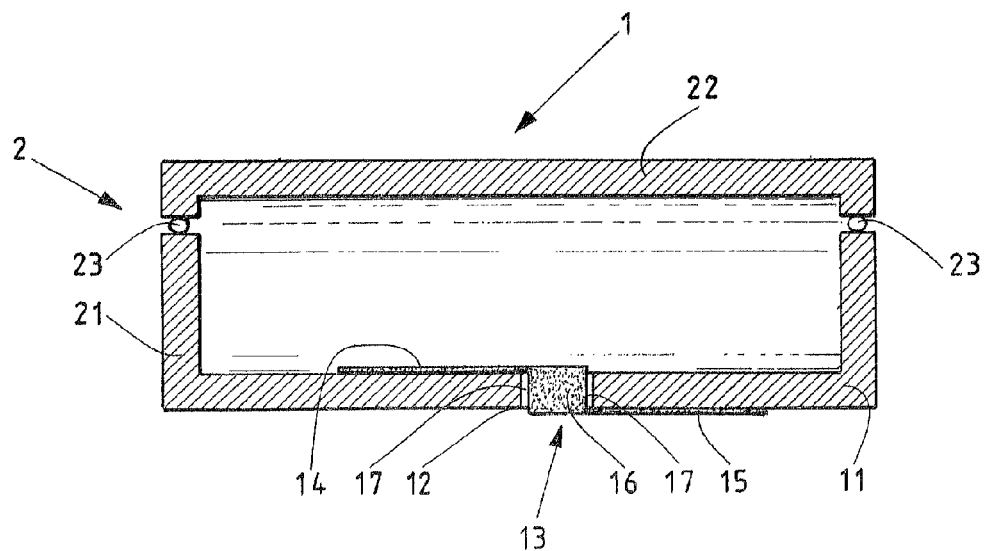
FIG. 1 schematically shows a cross-section of a housing of a surgical instrument, and FIG. 2 schematically shows a cross-section of a housing of a video endoscope according to another embodiment.

In the drawings, the same or similar types of elements and/or parts are provided with the same reference numbers so that a corresponding re-introduction can be omitted.

FIG. 1 schematically depicts the cross-section of a housing of a schematically indicated surgical instrument 1. A surgical instrument is for example provided by an endoscope, in particular a video endoscope, wherein the surgical instrument 1 has a hermetically sealed housing 2.

The housing 2 in the embodiment of the surgical instrument 1, for example as a video endoscope, is designed in this case as an elongated endoscope shaft, wherein on its distal end a window is provided, and a video camera is arranged as an optical image sensor unit behind the window in the interior of the housing 2 in the endoscope shaft.

In FIG. 1, the surgical instrument 1 is portrayed without fittings in the interior of the surgical instrument for reasons of clarity. The housing 2 consists of a plurality of housing parts. As shown in FIG. 1, the schematically portrayed housing 2 is formed with a pot-shaped basic body 21 and a cover body 22.

For example, the basic body 21 and cover body 22 are manufactured of ceramic, wherein the two housing parts are connected to each other by using active soldering, whereby active soldering 23 is formed in the region of the contact points between the basic body 21 and the cover body 22. The active soldering 23 is thereby formed between the basic body 21 and the cover body 22. The housing 2 of the surgical instrument 1 is thereby hermetically designed such that the sealed housing 2 is liquid-tight and/or steam-tight which correspondingly protects the optical and electronic components in the interior of the housing 2, even during hot steam sterilization, of for example a surgical instrument 1 designed as a video endoscope.

The basic body 21 portrayed in FIG. 1 has a housing wall 11, wherein a via 13 is formed in the bottom side in a penetration or opening 12 in the housing wall 11. The filled via 13 is also termed a "plugged vertical interconnect access (via)" and is an electrical connection between an electrical conductor path 14 formed on the inside of the basic body 21 or respectively on the inside of the housing wall 11, and an electrical conductor path 15 formed on the outside of the housing wall 11.

The via 13 is filled with a filling material 16 that consists of a metal in the embodiment portrayed in FIG. 1, wherein an electrical contact is established between the conductor path 14 and the conductor path 15 due to the electrically conductive filling material 16. A hermetically sealed housing 2 is formed due to the filling of the opening 12, wherein electrical lines are connected to the conductor paths, 14, 15.

Since the filling material 16 consisting of metal is electrically conductive in the exemplary embodiment in FIG. 1, a layer 17 is formed between the filling material 16 and housing wall to provide metallization for the solder or filling material 16. In addition, the via 13 is electrically insulated from the basic body 21.

The conductor paths 14, 15 can be designed as corresponding conductor path structures, wherein the conductor path structures are applied by means of printing, CVD methods (chemical vapor deposition methods), magnetic sputtering, laser ablation and the like.

In addition, it is also possible to form the conductor paths 14, 15 on the inside and outside of the housing wall 11 of the basic body 12 using so-called MIP technology or the laser direct structuring method (LDS method). When using MIP technology, electronic connections such as pins are arranged or respectively integrated in a base body such as a basic body 12 before a sintering process, wherein a metal layer is applied on the body after the sintering process. This can be done for example using deposition sputtering. Then the applied metal layer is structured to produce the conductor paths. The conductor paths can be reinforced electrochemically in another manufacturing procedural step.

In the laser direct structuring method, the electrical contacts that are for example designed as pins can be extrusion-coated with a plastic, and the conductor pattern can be transferred to the plastic using the LDS method. The electrochemical deposition of conductor paths can then occur at the previously exposed sites. In addition, it can also be provided that the conductor paths are connected to the contact points such as pins in additional steps.

Figure 2:
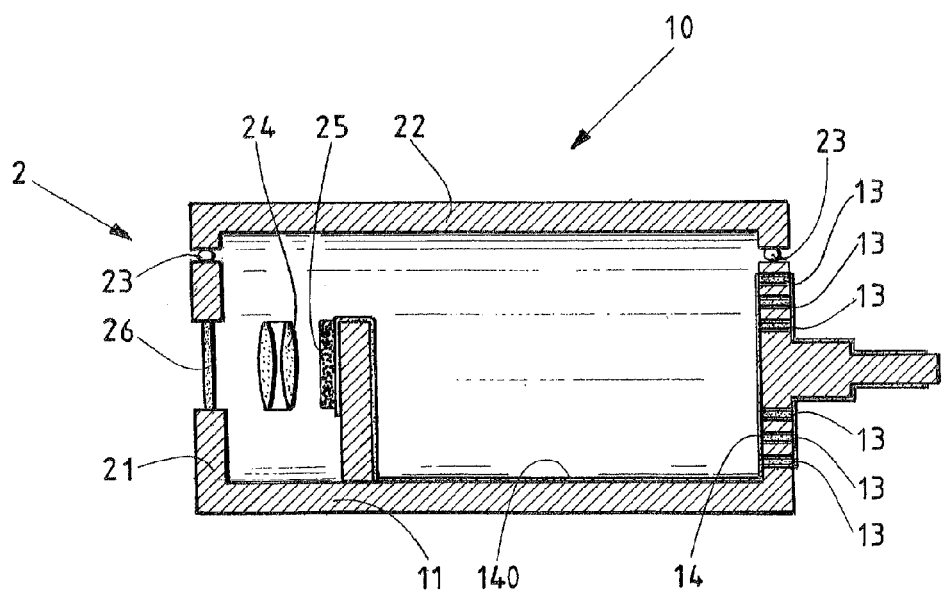

FIG. 2 schematically portrays a cross-section of an embodiment of a video endoscope 10, wherein the video endoscope 10 has a housing 2 designed as an elongated endoscope shaft with a basic body 21 and a cover body 22. The contact points between the basic body 21 and the cover body 22 are hermetically connected to each other by means of an active soldering 23.

At the distal end of the video endoscope 10, a window 26 is provided in the basic body 21, wherein a lens system 24 and an image sensor unit 25 are arranged behind the window 26 in the interior of the housing 2 at the distal end in order to record images from the exterior surroundings at the distal end of the video endoscope 10. In particular, the image sensor unit 25 is designed as a video camera or CCD camera.

At the proximal end of the housing 2 of the video endoscope 10 designed as an endoscope shaft, a plurality of vias 13 are formed in the face of the proximal end region, wherein the vias 13 are hermetically filled with a filling material. Each of the vias 13 is electrically connected to a conductor path on the outside of the housing wall 11 of the basic body 21, and to a conductor path in the interior of the housing 2. The penetrations 13 are designed corresponding to the principal depicted in FIG. 1.

In the interior of the housing 2, the conductor paths connected to the vias 13 are arranged on the inner wall of the housing in the longitudinal extension of the housing 2 designed as an endoscope shaft in order to form an electrical connection for example with the image sensor unit 25. The conductor paths in the longitudinal extension of the housing 2 between the proximal end region and the distal region of the video endoscope 10 are schematically identified with reference number 140 and connect the image sensor unit 25 to the electrical contacts outside of the hermetic housing 2 by means of the conductor paths 14 and the vias 13.

All named characteristics, including those to be taken from the drawings alone, and individual characteristics, which are disclosed in combination with other characteristics, are considered individually and in combination as essential to the invention. Embodiments according to the invention can be fulfilled through individual characteristics or a combination of several characteristics.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE LIST

1 Surgical instrument
2 Housing
10 Video endoscope
11 Housing wall
12 Opening
13 Via
14 Conductor path
15 Conductor path
16 Filling material
17 Layer
21 Basic body
22 Cover body
23 Active soldering
24 Lens system
25 Image sensor unit
26 Window
140 Conductor paths

The invention claimed is:

1. A surgical instrument comprising:
a housing having a housing wall, the housing wall having an interior and exterior surface, the interior surface defining a hermetically sealed interior, the housing wall further having a vertical interconnect access (via) to electrically connect an interior electrical contact formed to extend on the interior surface of the housing wall with an exterior electrical contact formed to extend on the exterior surface of the housing wall,
the via has a penetration in the housing wall, and the penetration is filled with a filling material to form the hermetically sealed interior,
the interior and exterior electrical contacts are formed as at least one electrically conductive conductor path on the interior surface of the housing wall and as at least one electrically conductive conductor path on the exterior surface of the housing wall,
the at least one conductor path on the interior surface of the housing wall, and the at least one conductor path on the exterior surface of the housing wall are electrically connected to each other by means of the via, and
the filling material of the via consists of metal; and
the housing is configured as an endoscope shaft and the via is formed in the proximal end region of the endoscope shaft.

2. The surgical instrument according to claim 1, wherein the filling material is electrically conductive in the penetration.

3. The surgical instrument according to claim 2, wherein at least one conductor path is formed on the inside of the housing wall using one or more of an MIP method (microscopic integrated processing (MIPTEC)) and a laser direct structuring (LDS) method, and/or that at least one conductor path is formed on the outside of the housing wall using one or more of the MIP method and the laser direct structuring method.

4. The surgical instrument according to claim 2, further comprising an additional conductor path for an optical image sensor unit arranged in the hermetically sealed interior of the housing, the additional conductor path being arranged such that the optical image sensor unit and the via are connected to each other, wherein the additional conductor path is formed in the hermetically sealed interior of the housing on the housing wall along a longitudinal extension of the housing.

5. The surgical instrument according to claim 2, wherein the housing is formed of ceramic.

6. The surgical instrument according to claim 1, wherein at least one conductor path is formed on the inside of the housing wall using one or more of an MIP method (microscopic integrated processing (MIPTEC)) and a laser direct structuring (LDS) method, and/or that at least one conductor path is formed on the outside of the housing wall using one or more of the MIP method and the laser direct structuring method.

7. The surgical instrument according to claim 6, further comprising an additional conductor path for an optical image sensor unit arranged in the hermetically sealed interior of the housing, the additional conductor path being arranged such that the optical image sensor unit and the via are connected to each other, wherein the additional conductor path is formed in the hermetically sealed interior of the housing on the housing wall along a longitudinal extension of the housing.

8. The surgical instrument according to claim 6, wherein the housing is formed of ceramic.

9. The surgical instrument according to claim 1, further comprising an additional conductor path for an optical image sensor unit arranged in the hermetically sealed interior of the housing, the additional conductor path being arranged such that the optical image sensor unit and the via are connected to each other, wherein the additional conductor path is formed in the hermetically sealed interior of the housing on the housing wall along a longitudinal extension of the housing.

10. The surgical instrument according to claim 9, wherein the housing is formed of ceramic.

11. The surgical instrument according to claim 9, wherein the optical image sensor unit is a video camera.

12. The surgical instrument according to claim 1, wherein the housing is formed of ceramic.

13. The surgical instrument according to claim 1, wherein the housing includes one or more of optical and electrical devices within the hermetically sealed interior of the housing.

14. The surgical instrument according to claim 1, wherein the filling material is electrically conductive in the penetration.

15. The surgical instrument according to claim 1, wherein at least one conductor path is formed on the inside of the housing wall using one or more of an MIP method (microscopic integrated processing (MIPTEC)) and a laser direct structuring (LDS) method, and/or that at least one conductor path is formed on the outside of the housing wall using one or more of the MIP method and the laser direct structuring method.

16. The surgical instrument according to claim 1, further comprising an additional conductor path for an optical image sensor unit arranged in the hermetically sealed interior of the housing, the additional conductor path being arranged such that the optical image sensor unit and the via are connected to each other, wherein the additional conductor path is formed in the hermetically sealed interior of the housing on the housing wall along a longitudinal extension of the housing.

17. The surgical instrument according to claim 1, wherein the housing is formed of ceramic.

18. The surgical instrument according to claim 1, wherein the housing is formed of plastic.

19. The surgical instrument of claim 1, wherein the housing is a portion of one of an endoscope or video endoscope.

20. The surgical instrument of claim 1, wherein the housing being formed by a concave portion and a cover portion covering the concave portion, wherein the concave portion and cover portion are hermetically sealed to each other with active soldering disposed at contact points between the concave portion and the cover portion to form the hermetically sealed interior.

* * * * *